United States Patent
Boileau et al.

(10) Patent No.: US 6,171,341 B1
(45) Date of Patent: Jan. 9, 2001

(54) PROSTHESIS FOR THE UPPER EXTREMITY OF THE HUMERUS

(75) Inventors: Pascal Boileau, Nice; Gilles Walch, Lyons, both of (FR)

(73) Assignee: Tornier SA, Saint-Ismier (FR)

(*) Notice: Under 35 U.S.C. 154(b), the term of this patent shall be extended for 0 days.

(21) Appl. No.: 08/901,534

(22) Filed: Jul. 28, 1997

(30) Foreign Application Priority Data

Aug. 2, 1996 (FR) .................................................. 96 09976

(51) Int. Cl.$^7$ ......................................................... A61F 2/40
(52) U.S. Cl. ......................................................... 623/19.11
(58) Field of Search ........................................ 623/19, 23

(56) References Cited

U.S. PATENT DOCUMENTS

| | | |
|---|---|---|
| 3,228,393 | 1/1966 | Michele . |
| 3,320,951 * | 5/1967 | Wittebol ................................ 623/23 |
| 4,865,605 * | 9/1989 | Dines et al. ........................... 623/19 |
| 4,919,670 * | 4/1990 | Dale et al. ............................. 623/19 |
| 4,938,771 * | 7/1990 | Vecsei et al. ......................... 623/23 |
| 5,019,108 | 5/1991 | Bertin et al. . |
| 5,489,309 * | 2/1996 | Lackey et al. ........................ 623/19 |
| 5,658,340 * | 8/1997 | Muller et al. ......................... 623/23 |
| 5,725,161 * | 3/1998 | Camino et al. ....................... 623/19 |

FOREIGN PATENT DOCUMENTS

| | | | |
|---|---|---|---|
| 2689758 | 4/1992 | (FR) . | |
| 2689758 * | 10/1993 | (FR) | ................................... 623/19 |
| 1340451 | 1/1972 | (GB) . | |
| 0555629A1 * | 8/1993 | (WO) | .................................. 623/23 |

OTHER PUBLICATIONS

Zimmer Catalog, Warsaw, Ind., Feb. 1973.*

* cited by examiner

*Primary Examiner*—V. Millin
*Assistant Examiner*—Alvin Stewart
(74) *Attorney, Agent, or Firm*—Dowell & Dowell, P.C.

(57) ABSTRACT

A humeral prosthesis of such a type that is provided with a rod intended to be anchored in the humeral canal of a patient, a metaphyseal element extending the rod upward and towards the inside, being this metaphyseal element attached at an area of connection to a flange that serves as support for a generally hemispheric cap capable of interacting with the shoulder socket. The area of connection is arranged approximately along a median line of the mentioned flange and the area of connection extends only over a portion of the mentioned median line so as to establish outside of the area of connection, or outside of a portion of the area of connection, a clearance zone for the joining and fusing of the osseous fragments of the metaphysis.

5 Claims, 2 Drawing Sheets

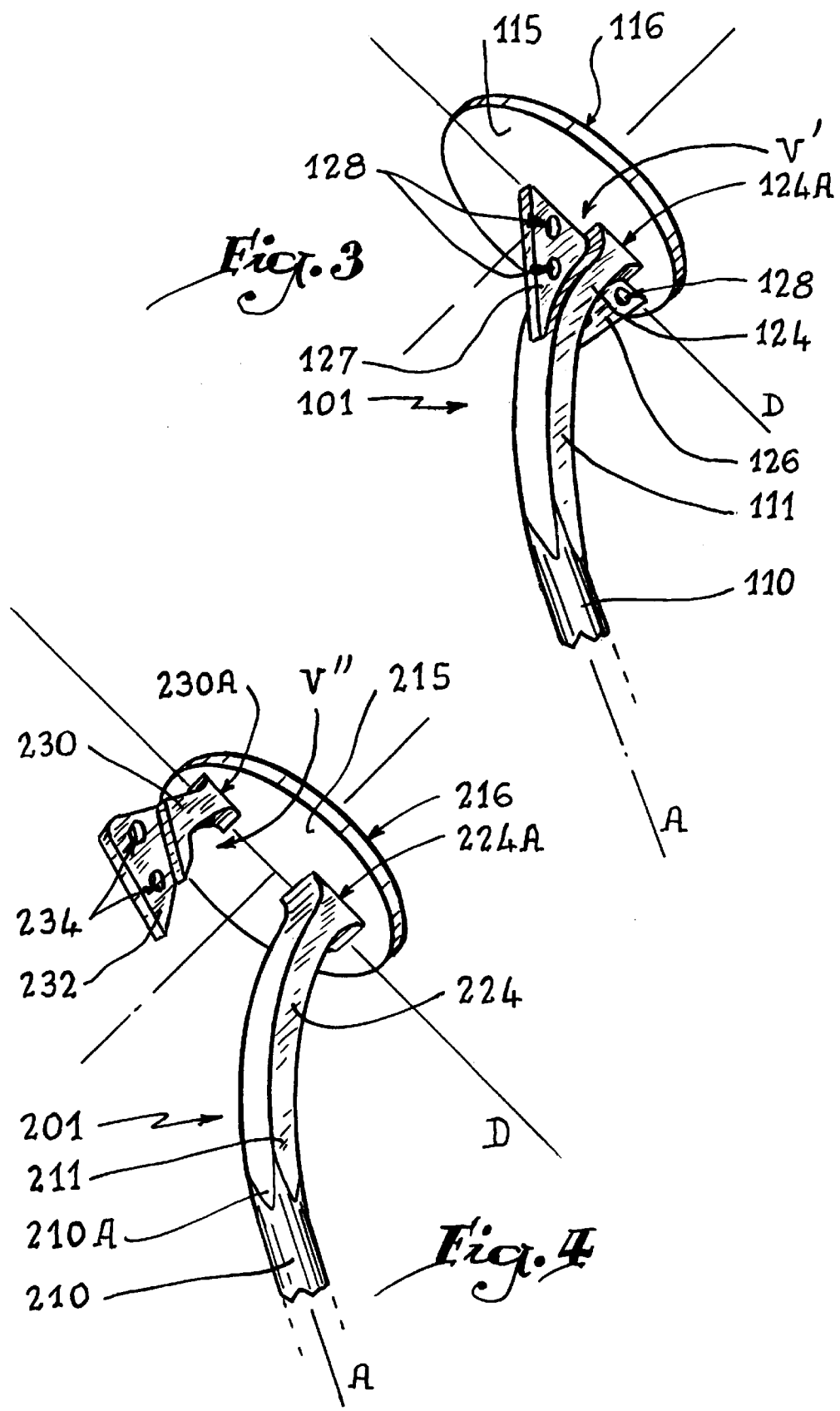

PROSTHESIS FOR THE UPPER EXTREMITY OF THE HUMERUS

BACKGROUND OF THE INVENTION

1. Field of the Invention

This invention relates to a type of humeral prosthesis that is provided with a rod to be anchored in the humeral canal of a patient, a metaphyseal element that extends upwards from said rod and towards the inside, this metaphyseal element being fitted, at an area of connection, to a flange against which rests an approximately hemispheric calotte or cap suitable to interact with the shoulder socket. The mentioned area of connection is arranged approximately along a median line of the flange.

2. History of the Related Art

When the upper extremity of the humerus is fractured, the humerus generally breaks into several pieces, in particular the shaft, the humeral tuberosities and, lastly, the head of the humerus that interacts with the shoulder socket.

When such a fracture is set, only the head of the humerus must be replaced by an approximately hemispheric cap, while the other fractured pieces may be set around a prosthesis.

Well known in the art are prosthesis of this type which, as a rule, comprise a rod, or shaft portion, that is inserted in the humeral canal of the shaft of the bone. This rod is extended by a metaphyseal element that is bent upwards and towards the inside of a prosthesis worn by a standing patient, around which prosthesis are brought together the tuberosities constituting the metaphysis of the bone with the intention of setting them. The metaphyseal element of the prothesis is joined to a flange of the seat of a cap replacing the head of the humerus.

This type of protheses, such as, for example, those of NEER, present however certain disadvantages. In fact, they are made out of one only block which renders it necessary to have a large number of implants to meet the anatomic requirements of the different patients. Furthermore, these prosthesis have only one size of rod and of cap, and the latter cannot be offset as proven necessary in some cases. Moreover, the space of the upper portion of the prosthesis does not allow, in the case of serious fractures of the upper portion of the humerus, a satisfactory setting between the osseous fragments.

Furthermore, from French Patent A-2 689 758 is known a humeral prosthesis that comprises in its metaphyseal element a reinsertion flange. This flange is provided with perforations through which pass threads that ensure the anchoring of the bone to the prosthesis. However, the perforations of very slight diameter do not allow for the osseous fragments to come closer together. Thus, the mutual uniting of these fragments proves to be insufficient which, of course, is detrimental to the physical integrity of the patient.

SUMMARY OF THE INVENTION

Thus, the aim of the present invention is to produce a humeral prosthesis of aforementioned type that would overcome the above-mentioned disadvantages of the hitherto known prosthesis.

With this in mind, the invention relates to a humeral prosthesis of the mentioned type, characterized by the fact that the area of connection extends only over a portion of the median line in order to establish outside of the area of connection, or outside of a portion of the area of connection, a clearance zone for the joining and fusing of the osseous fragments of the metaphysis.

The invention allows the attaining of the above-mentioned objectives. In fact, the presence of a clearance zone allows the formation of a cluster of fragments or even the placing of a graft in order to facilitate the osteosynthesis subsequent to the surgical intervention. In comparison with the hitherto known prosthesis in which the osseous fragments of the metaphysis were attached only to the prosthesis, the prosthesis in accordance with the invention thus has the advantage that these osseous fragments could be brought together and be approximately attached to each other according to their crowding and their original configuration. This would allow a clearly better osseous uniting.

The joining and fusing clearance zone for the osseous fragments is located at the outside portion of the overall clearance zone of the metaphyseal element. As a matter of fact, it is this external proximal portion that seems to be the most difficult one to set because of the stress transfers to which this osseous portion is subjected during the normal shoulder action.

According to an advantageous aspect of the present invention, the median line of the flange is a diameter that is roughly co-planar with the rod's axis.

According to another aspect of the present invention, the metaphyseal element is provided with one branch extending the humeral rod and connecting it to the flange at the area of connection in order to constitute, outside the area of connection, the clearance zone for the joining and fusing of the fragments of the metaphysis.

This branch may be provided with a concavity oriented towards the inside. It can be provided with at least one fin thinner than this branch, oriented towards the inside and/or the outside, and provided with perforations. These perforations are intended for the passing of suture threads which would allow the anchoring of the osseous fragments to the prosthesis to obtain a better reconstruction. The fact that the fin is thinner than the only branch ensures a better positioning of the various osseous fragments with respect to each other, thus ensuring a close contact between them.

According to another aspect of the present invention, the metaphyseal element comprises two inside and outside branches that extend from the rod and are attached to the flange at the area of connection in order to constitute between these areas of connection a cavity that forms the mentioned clearance zone for the joining and fusing of the osseous fragments of the metaphysis. This outside branch constitutes a bearing surface for the spongy bones and avoids that they collapse.

In this case, the outside branch may be provided with a fin thinner than such branch that is oriented towards the outside and provided with perforations for the passing of suture threads.

According to an advantageous aspect of the present invention, the metaphyseal element is provided with one branch that extends from the humeral rod and is attached to the flange at an area of connection, as well as with a lug that protrudes from the flange in an opposite direction of the cap and, outside of the branch, the clearance for the joining and fusing of the fragments of the metaphysis is established between the area of connection of the branch and the area of connection of the lug. The presence of the lug avoids the collapsing of the spongy bone because of the bearing surface constituted by this lug. Furthermore, because this lug extends only to the humeral rod, the clearance zone for the joining and fusing of the osseous fragments of the metaphysis, established between the outside branch, the lug and the flange, opens at the rod. This clearance zone is thus of major dimensions allowing a satisfactory consolidation of the osseous fragments to each other.

The lug may be provided with a fin thinner than the lug, oriented towards the outside and provided with perforations intended for the passing of the suture threads.

BRIEF DESCRIPTION OF THE DRAWINGS

The present invention is explained below, making reference to the accompanying drawings shown only by way of example, but not limited thereto, and in which:

FIGS. 3 and 4 are perspective views analogous to FIG. 1, showing second and third embodiments of the invention.

DESCRIPTION OF THE PREFERRED EMBODIMENT

Figure 1:
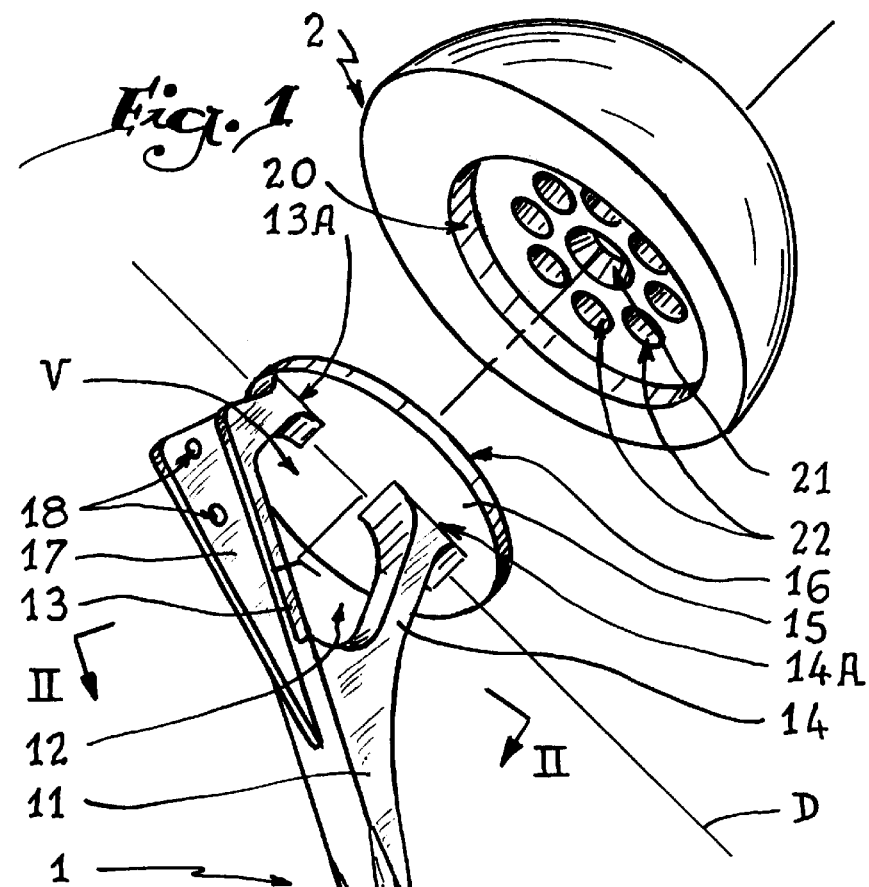
FIG. 1 shows an exploded perspective view, illustrating one form of embodiment of a humeral prosthesis in accordance with the invention.

The prosthesis shown in FIG. 1 and designated as a whole by reference number 1, is intended to carry a hemispheric cap 2 capable of interacting with the shoulder socket of a patient.

This prothesis is provided with a nearly round rod 10 that fits into the humeral canal, extended by a metaphyseal element 11 to which is attached a flange 15.

This metaphyseal element is provided with an outside branch 13 and an inside branch 14, each of which is attached to the flange by areas of connection 13A and 14A, respectively. These latter are approximately arranged along a median line of the flange, that is to say a diameter (D) arranged on the same plane (P) as the axis (A) of the rod 10 of the prosthesis. These areas of connection, 13A and 14A, extend only over a portion of this diameter in order to constitute between the branches 13 and 14 a cavity 12 that forms a clearance zone (V) for the joining and fusing of the osseous fragments of the metaphysis, in which clearance zone the splintered osseous fragments may be joined for their consolidation.

Furthermore, provisions can be made that, prior to inserting the rod 10 into the humeral canal, the cavity 12 be filled with osseous fragments or a substitute that is cut according to the contour of the cavity.

The flange 15 has a tilted side 16 that interacts with a round housing 20 provided in the flange, that is eccentric with respect to the axis of the flange itself. The diameter of this housing corresponds more or less to that of the mentioned flange. In the center of this housing is arranged a truncated bore 21, the profile of which corresponds to that of a not shown piece affixed to the flange 15. A number of holes 22 are provided at the bottom of the housing 20, at the external periphery of the bore 21.

Figure 2:
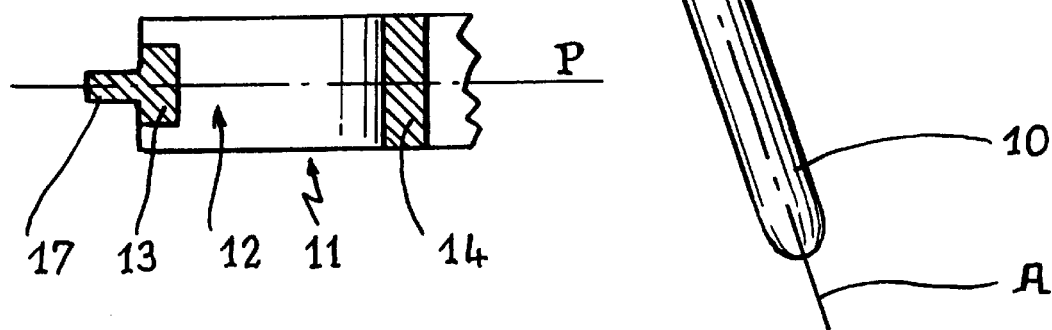
FIG. 2 shows a section along the line II—II of FIG. 1.

As especially shown in FIG. 2, the outside branch 13 has a smaller than that of branch 14 in order to ensure a better joining of the osseous fragments when the rod 10 is inserted into the humeral canal. This outside branch 13 does also provide support to the spongy bones so as to hinder their collapsing.

The outside branch 13 extends towards the outside by means of a fin 17 whose transversal dimension is smaller than that of the branch 13. This fin is provided with perforations 18 allowing the passing of suture threads.

FIG. 3 shows a second embodiment of the prosthesis in accordance with the present invention. In this figure, the elements that are similar to those of the embodiment of FIGS. 1 and 2 are referenced by the same numbers increased by 100.

The prosthesis 101 differs from the prosthesis 1, illustrated in FIG. 1, in that its metaphyseal element 111 is not constituted by two branches but rather by one only branch 124 whose concavity is oriented towards the inside. This only branch 124 extends the rod 110 in such a manner that it is affixed to the flange at the level of an area of connection 124A that is arranged approximately along the diameter (D) of the flange, coplanar with the axis (A) of the rod 110 of the prosthesis. This area of connection 124A extends only over a portion of this diameter so as to establish outside of the branch 124 a clearance (V') for the joining and fusing of the osseous fragments of the metaphysis.

One inside fin 126 and one outside fin 127 protrude from the face of the flange opposite to the face 16 of reception of the cap 2. Each of these fins 126 and 127 extend as far as the outside and inside faces, respectively, of the only branch 124. The transversal dimensions of these fins are clearly smaller than those of the branch 124 so as to enable an easier joining of the osseous fragments. Each of these fins is provided with perforations 128 intended for the passing of the suture threads. Of course, it would be possible to provide in the proximity of the branch 124 only the outside fin 127 or only the inside fin 126.

FIG. 4 shows a third embodiment of the prosthesis in accordance with the present invention. In this third embodiment, the elements that are similar to those described in FIGS. 1 and 2 are referenced by the same numbers increased by 200, while the elements similar to those illustrated in FIG. 3 are referenced by the same numbers increased by 100.

The prosthesis illustrated in FIG. 4 differs from that of FIG. 3 in that the branch 224 is not provided with fins. The metaphyseal element 224 of the prosthesis 201 is completed by a lug 230 that protrudes from outside of the flange in an opposite direction of the cap 2. The branch 224 and the lug 230 are attached to the flange 215 by two areas of connection 224 and 230A, respectively. These latter are arranged approximately along the diameter (D) of the flange, co-planar with the axis (A) of the rod 210 of the prosthesis. These areas of connection extend only over a portion of this diameter in order to constitute between the branch 224 and the lug 230 a clearance zone (V") for the joining and fusing of the osseous fragments of the metaphysis.

The lug 230 is extended by a fin 232 flaring out in direction of the rod 210. The transversal dimensions of this fin 232 are smaller than those of the lug 230 and it is provided with perforations 234 that allow the passing of the suture threads.

Due that the lug does not extend to the proximal portion 210A of the rod 210, the clearance zone (V") for the joining and fusing of the fragments is open at this portion 210A. Furthermore, the presence of the lug 230 ensures a support for the spongy bones and hinders their collapsing.

What we claim is:

1. A humeral prosthesis comprising;
   a rod adapted to be anchored in a humeral cavity of a patient,
   a metaphyseal element extending from said rod and including an inside branch and an outside branch which are spaced from one another and each having an end portion and at least said inside branch being an extension of said rod,
   said end portions being directly connected to a planar lower jaw face of a flange at areas of connection which are in spaced relationship with respect to one another so as to extend only along a portion of a median line of said flange so as to define an open zone therebetween for fusing of osseous fragments of the metaphysis and which open zone is defined by a portion of said planar lower face of said flange located between said areas of connection of said end portions, a hemisphere cap connected to said flange, each of said first and second branches having a cross-sectional dimension, a fin extending along a portion of said outside branch remote from said cavity, said fin having a cross-sectional dimension which is less than said cross-sectional dimension of said outside branch, and a plurality of spaced openings in said fin for receiving suture threads therethrough.

2. A prosthesis in accordance with claim 1 wherein said median line of said flange is a diameter of said flange generally co-planar with a central elongated axis of said rod.

3. The humeral prosthesis if claim 1 wherein both said inside and outside branches are extensions of said rod and said outside branch being concave toward said open zone for fusing osseous fragments of the metaphysis.

4. A humeral prosthesis comprising;

a rod adapted to be anchored in a humeral canal of a patient, a metaphyseal element extending from said rod to an end portion which is connected to a a flange along a portion of a median line thereof, a lug having an end portion connected to said flange in spaced relationship with respect to said end portion of said metaphyseal element so as to define between said lug and said metaphyseal element a zone for fusing of osseous fragments of the metaphysis, and said lug having a free end spaced from said flange and spaced from said metaphyseal element, and a hemispherical cap connected to said flange on a face opposite said lug and said metaphyseal element.

5. The prothesis of claim 4 wherein said lug has a cross-sectional thickness dimension, a fin extending from said lug and having openings therein, said fin having a cross-sectional dimension which is less than the cross-sectional dimension of said lug.

\* \* \* \* \*